United States Patent [19]

Nanjo

[11] Patent Number: 5,382,988
[45] Date of Patent: Jan. 17, 1995

[54] STEREOSCOPIC RETINAL CAMERA WITH FOCUS DETECTION SYSTEM

[75] Inventor: Tsuguo Nanjo, Toyohashi, Japan

[73] Assignee: Nidek Co., Ltd., Japan

[21] Appl. No.: 95,763

[22] Filed: Jul. 23, 1993

[30] Foreign Application Priority Data

Jul. 31, 1992 [JP] Japan .................. 4-224894
Oct. 30, 1992 [JP] Japan .................. 4-316405
Apr. 15, 1993 [JP] Japan .................. 5-114057

[51] Int. Cl.$^6$ ............... A61B 3/14; A61B 1/04
[52] U.S. Cl. ...................... 351/206; 351/211; 351/221; 354/62
[58] Field of Search ............. 354/62; 351/206, 211, 351/221, 205; 250/201.7

[56] References Cited

U.S. PATENT DOCUMENTS

| | | | |
|---|---|---|---|
| 4,436,388 | 3/1984 | Takahashi et al. | 354/62 X |
| 4,452,517 | 6/1984 | Kohayakawa | 354/62 X |
| 5,120,122 | 6/1992 | McAdams | 351/206 |
| 5,255,026 | 10/1993 | Arai et al. | 351/206 |

FOREIGN PATENT DOCUMENTS

| | | | |
|---|---|---|---|
| 53-43277 | 11/1978 | Japan . | |
| 0099652 | 8/1979 | Japan | 351/206 |
| 61-39050 | 9/1986 | Japan . | |
| 4-71528 | 3/1992 | Japan | 351/206 |
| 4-183434 | 6/1992 | Japan | 354/62 |
| 5-123299 | 3/1993 | Japan | 351/206 |

Primary Examiner—William L. Sikes
Assistant Examiner—David R. Parsons
Attorney, Agent, or Firm—Parkhurst, Wendel & Rossi

[57] ABSTRACT

A stereoscopic retinal camera is provided with an illumination optical system for illuminating the fundus of an examinee's eye, an observing/photographing optical system for observing and photographing an image of the fundus of the eye in a stereoscopic picture, which includes a light beam splitting optical system for splitting the light beam of the illumination optical system reflected by the fundus into a right light beam and a left light beam and a pair of image forming optical systems for forming respective images of the fundus by the two light beams, an index projecting optical system for projecting a focusing index on the examinee's eye, an index detecting optical system for detecting the focusing condition of the focusing index projected on the fundus of the eye, a judging means for judging a focusing condition by processing signals provided by the index detecting optical system, wherein one of the index projecting optical system and the index detecting optical system comprises a pair of right and left optical systems, which are disposed on each light path branched from light paths of the image forming optical systems, and use a part of the light path of the image forming optical system in common with a reflecting mirror for reflecting the images of the index.

17 Claims, 11 Drawing Sheets

STEREOSCOPIC RETINAL CAMERA WITH FOCUS DETECTION SYSTEM

BACKGROUND OF THE INVENTION

1. Field of the Invention

The present invention relates to a stereoscopic retinal camera, and more particularly to a focus detecting system to be equipped in a stereoscopic retinal camera.

2. Description of Related Art

In focusing a conventional retinal camera on the fundus of an examinee's eye, a linear reticule of an observing system is superposed on a spatial image of the retina, and the focusing condition of the spatial image is observed by the observing system.

A monocular retinal camera has been proposed in Japanese Patent Publication No. SHO 61(1986)-39050, in which an index projecting system is disposed in an optical path branched from an optical path of a photographing optical system.

Referring to FIG. 11, the monocular retinal camera is provided with a light path dividing means disposed behind a perforated mirror and an index projecting system disposed in the optical path branched by the light path dividing means, by which an image of an index is projected to the fundus of the eye.

More specifically, an index projecting system C is disposed in the optical path branched from an optical path of a photographing optical system A by a reflecting mirror 45 which is the light path dividing means, whereby the focusing operation of the retinal camera on the fundus of the examinee's eye is not affected by illuminating condition, the index projecting system C and the photographing optical system A may be simply interlocked so that both focal parts thereof are moved together. In the camera, index projecting system C projects an infrared light beam on the fundus $E_R$ of the eye without using mydriatica or the like to the eye, and whether the infrared image of the index is in or out of focus on the fundus $E_R$ is judged. Accordingly, the alignment of the camera to the fundus of the eye can be achieved with a simple and easy mechanism.

Japanese Patent Publication No. SHO 53(1978)-43277 also discloses another monocular retinal camera in which an index projecting system is disposed in an optical path branched from an optical path of an illumination optical system.

Referring to FIG. 12, the retinal camera is provided with a photographing system A for photographing an image of a fundus $E_R$ of an eye, an illumination system B for irradiating an infrared beam on the fundus $E_R$ via a light path dividing means 55 arranged in the optical path of the photographing system A, a focus index projecting system C for projecting a plurality of focusing infrared beams emerging from a focus index 60 on the fundus $E_R$, which is movable in relation with the photographing system A, and an observing system D including an infrared image display means 65 in which an infrared light image reflected by the fundus is converted into a visible image, each system B, C and D using the optical path of the photographing system A in common.

In the retinal camera, a fundus image and a focusing index image formed by the both infrared light beams, reflected by the fundus are converted into visible images through the observing system. Then the photographing system A is moved so as to change a direction of the optical axis relatively to the fundus to determine a photographing visible field while the fundus is observed, and the focusing index projecting system C interlocking with the photographing system A is adjusted so that the plurality of focus index images coincide with one shape focus index image, accordingly, the photographing system A may be focused on the fundus of the eye.

However, in the former retinal camera, the observing condition, i.e., the condition of the image, is directly dependent on the diopter, i.e., the refracting power of the eyes of the observer, accordingly, the refracting power of a view finder should be exactly adjusted and precise alignment needs highly skillful and experienced technique.

In the latter retinal camera, the index projecting light beam passing through the space between the illuminating light beam and the photographing light beam or overlap part of the illuminating light beam, which makes adjustment of the optical system difficult. And, it is also difficult to manufacture and adjust the retinal camera because the light path dividing means for the index projecting system has to be disposed so as not to eclipse the optical path of a focus lens in the photographing optical system. Additionally, if the construction is applied to a stereoscopic retinal camera which needs two photographing luminous flux, it is foreseen that its constitution may become too complex.

Further, the latter retinal camera is applied to a monocular retinal camera, alternatively in a case that the camera is applied to a stereoscopic retinal camera to obtain two picture images having different parallax in right and left pictures, the following problem may be occurred. Namely, two photographing optical axes, for photograph of a fundus with the stereoscopic retinal camera, are often in eccentricity different from a cornea and a crystalline lens, accordingly, the latter retinal camera as it is may not obtain stereoscopic image of the fundus to be observed by the stereoscopic retinal camera. There is no idea about how the stereoscopic optical system may be utilized in the latter retinal camera, and in what focussing condition each of right and left stereoscopic images should be, accordingly, adaptability of the latter construction to the stereoscopic retinal camera is not sufficient.

SUMMARY OF THE INVENTION

The present invention has been made in view of the above circumstances and has an object to overcome the above problems and to provide a stereoscopic retinal camera of practical use, which is capable of easily aligning, and checking a focusing condition of right and left images of a fundus.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a stereoscopic retinal camera of this invention comprises an illumination optical system for illuminating the fundus of an examinee's eye, an observing/photographing optical system for observing and photographing an image of the fundus of the eye in a stereoscopic picture, and comprising (a) a light beam splitting optical system for splitting the light beam of the illumination optical system reflected by the fundus into a right light beam and a left light beam and (b) a pair of image forming optical systems for forming respective images of the fundus by the two light beams, an index projecting optical system for projecting a focusing index on the examinee's eye, an index detecting optical system for detecting the focusing condition of the focusing index projected on the fundus of the eye, a judging means for judging a focusing condition by processing signals provided by the index detecting optical system, wherein one of the index projecting optical system and the index detecting optical system comprises a pair of right and left optical systems, the pair of optical systems are disposed on each light path branched from light paths of the image forming optical systems, and use a part of the light paths of the image forming optical system in common with a reflecting mirror for reflecting the images of the index.

BRIEF DESCRIPTION OF THE DRAWINGS

The accompanying drawing, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of several preferred embodiments of a stereoscopic retinal camera with a focus detecting device embodying the present invention will now be given referring to the accompanying drawings.

Figure 1:
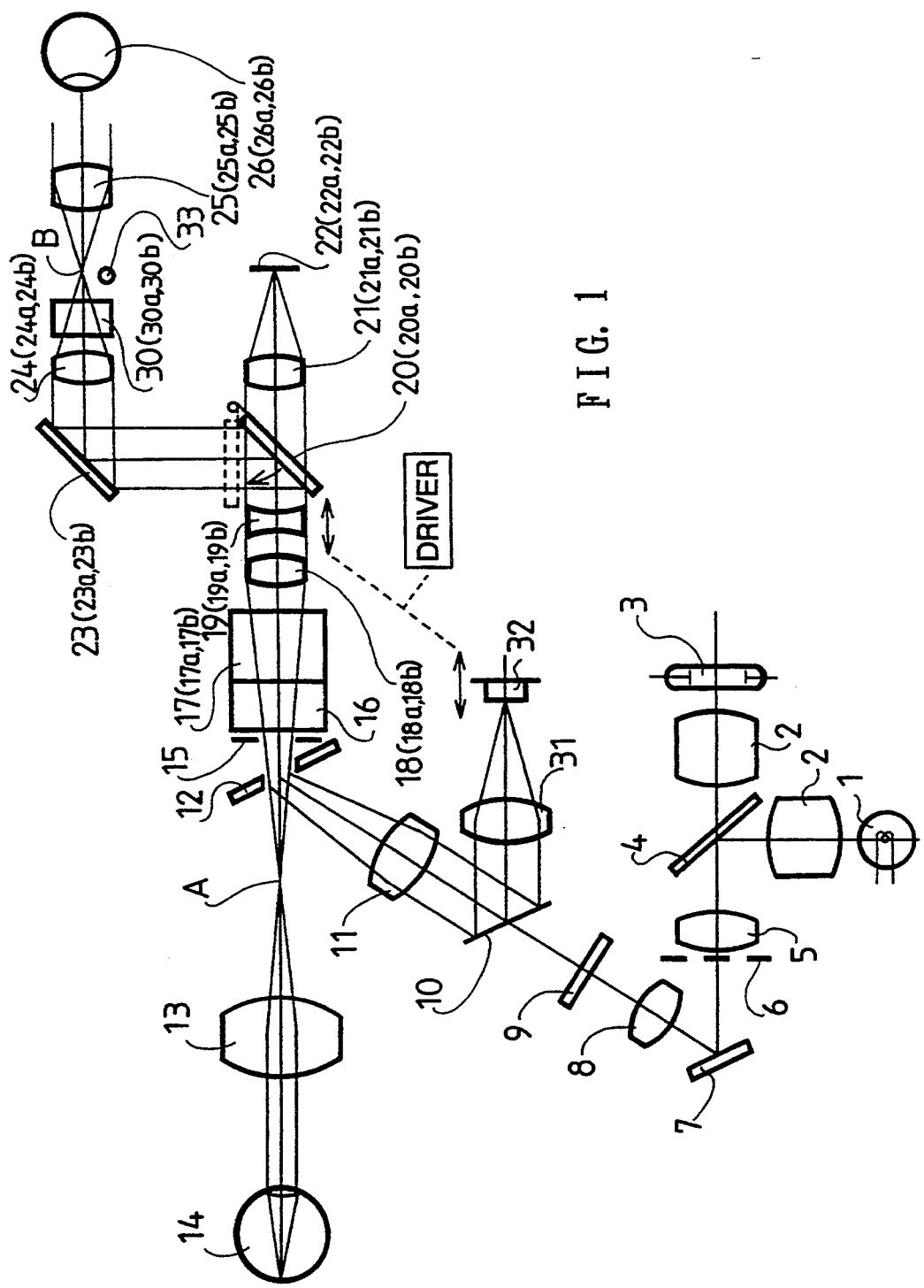
FIG. 1 is a diagrammatic side view of the optical system of a stereoscopic retinal camera in a first embodiment according to the present invention, except for an index projecting system.

A stereoscopic retinal camera in a first embodiment according to the present invention, as shown in FIG. 1, mainly comprises an illumination optical system, a photographing optical system, an observing optical system, an index projecting optical system and a focusing detecting optical system.

(Illumination Optical System)

More specifically, the illumination optical system is provided with a halogen lamp 1, i.e., an observing light source, condenser lenses 2, a xenon flash lamp 3, i.e., a photographing light source, a beam splitter 4, a relay lens 5, an aperture diaphragm 6 having a circular slit, a mirror 7 for deflecting a light path, an illuminating relay lens 8, an index plate 9 provided with a central black point to eliminate detrimental light, a beam splitter 10 for transmitting a light beam emerged from the halogen lamp 1 and for reflecting a light beam reflected by the fundus of the eye 14, which is a component of the focus detecting optical system, an illuminating relay lens 11, a perforated mirror 12 and an objective lens 13. The halogen lamp 1 and the xenon flash lamp 3 are in a conjugate relation with respect to the condenser lenses 2.

The aperture diaphragm 6 is provided with a circular slit for restricting the illumination light beam emerged from the halogen lamp 1 in a circular slit space. An intermediate image of the slit is formed near the opening of the perforated mirror 12, the intermediate image of the slit is reflected by the perforated mirror 12 and the objective lens 13 focuses the image of the slit near the cornea to illuminate the fundus of the eye 14.

(Photographing Optical System)

Figure 2:
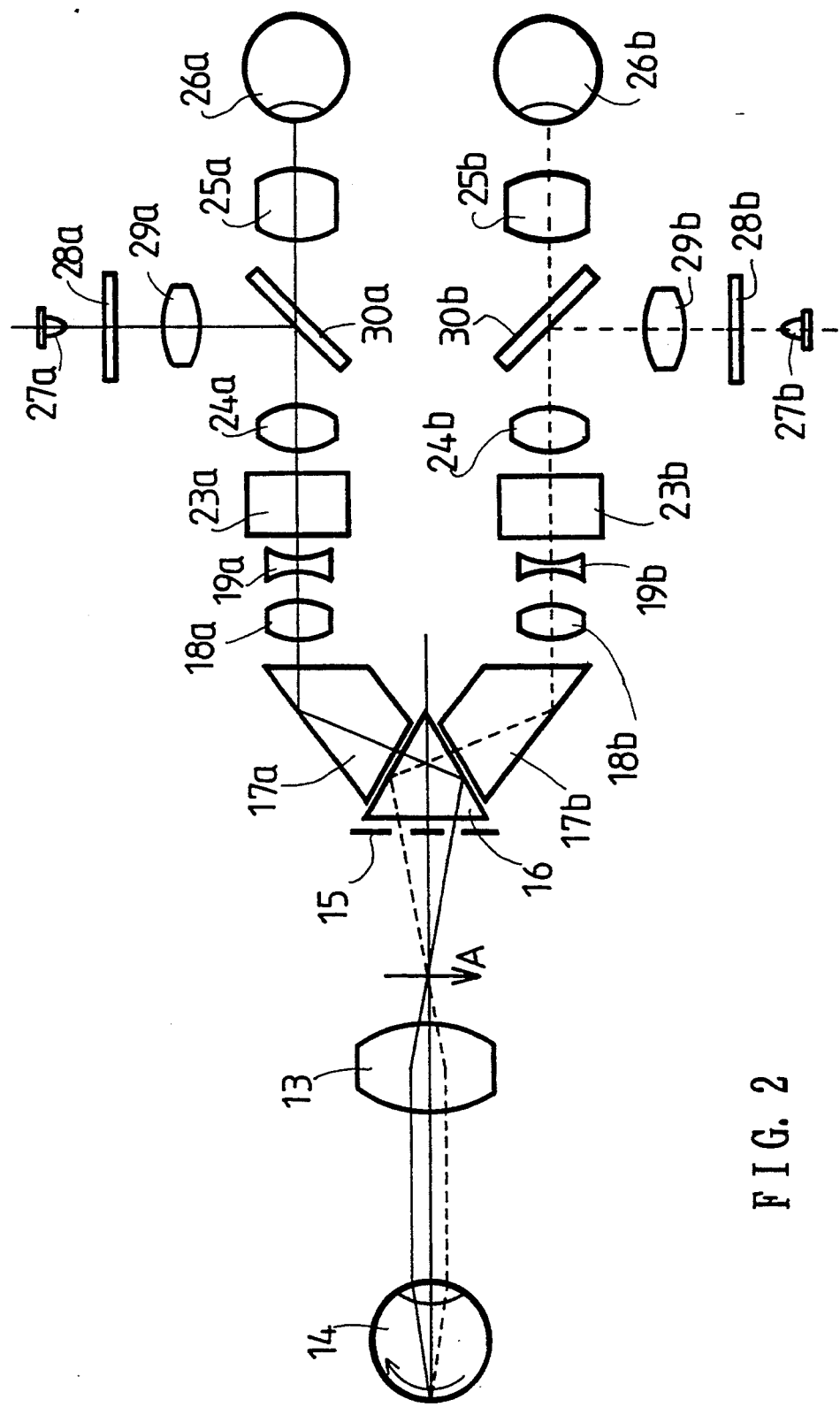
FIG. 2 is a diagrammatic top view of the optical system of FIG. 1.

The photographing optical system is provided with the objective lens 13, a two-hole diaphragm 15 for dividing the light beam reflected by the fundus into two light beams as shown in FIG. 2, a light beam splitting prism 16 for interchanging a right light beam and a left light beam, light beam splitting prisms 17(17a, 17b) for collimating the two light beams so that the collimated light beams pass along two parallel paths separated from each other by a designated distance, relay lenses 18(18a, 18b) disposed respectively on each light path of the two divided light beams, focusing lenses 19(19a, 19b), image forming lenses 21(21a, 21b), and films 22(22a, 22b).

A two-hole diaphragm 15 is in a conjugate relation with the pupil of the eye 14 with respect to the objective lens 13.

The light beam reflected by the fundus of the examinee's eye 14 is focused at point A an inverted image by the objective lens 13, passes through the opening of the perforated mirror 12, the two-hole diaphragm 15, the prisms 16, 17(17a, 17b), the relay lenses 18(18a, 18b), focusing lenses 19(19a, 19b) and image forming lenses 21(21a, 21b). The image forming lenses 21(21a, 21b) form respectively the images, i.e., a right image and a left image, of the fundus on the films 22(22a, 22b). The focusing lenses 19(19a, 19b) are movable along the optical axis of the photographing optical system. The positions of the focusing lenses 19a and 19b are adjusted according to the refractive power of the examinee's eye 14 to focus the images of the fundus on the films 22(22a, 22b).

Swing mirrors 20(20a, 20b), arranged on each light path of the two light beams, can be turned between a position to reflect the light beam toward the observing optical system and a position to allow the light beam to pass along the optical axis of the photographing optical system to the films 22. In photographing the picture of the fundus, the swing mirrors 20a and 20b are turned up in the direction of the arrow shown in FIG. 1 in synchronism with the flashing action of the xenon flash lamp 3 to allow the light beams reflected by the fundus to fall on the films 22.

(Observing Optical System)

The observing optical system and the photographing optical system use the objective lens 13, the swing mirrors 20(20a, 20b) and the components between the objective lens 13 and the swing mirrors 20 in common, further the observing optical system comprises mirrors 23(23a, 23b), observing image forming lenses 24(24a, 24b) and oculars 25(25a, 25b).

When observing the fundus, the swing mirrors 20 are set on the light paths of the photographing optical system to reflect the observing light beams reflected by the fundus and passed through the components from the objective lens 13 through the focusing lenses 19 toward mirrors 23a and 23b, which makes the individual light paths of the observing optical system separate from the path of the photographing system. The observing light beams reflected by the mirrors 23a and 23b passes through observation image forming lenses 24a and 24b, and oculars 25a and 25b, and fall on the right eye 26a and the left eye 26b of the observer.

The light beam emerging from the halogen lamp 1 passes the objective lens 13, the opening of the perforated mirror 12 after being reflected by the fundus, and is split into two light beams by the light beam splitting prism 16 which interchanges the right light beam and the left light beam. The two light beams are collimated by the prisms 17(17a, 17b) respectively so as to pass along two parallel paths, and each of the light beams passes through the relay lenses 18(18a, 18b), the focusing lenses 19(19a, 19b), and is deflected by the swing mirrors 20(20a, 20b) toward the mirrors 23(23a, 23b). Each of the light beams reflected by the mirrors 23(23a, 23b) is focussed at a point B in an erect image by the image forming lenses 24(24a, 24b). The image of the fundus of the eye 14 are observed in an erect image through the oculars 25(25a, 25b).

(Focusing Detecting Optical System)

The focusing detecting optical system consists of an index projecting system and an index detecting system.

(a) Index projecting system

The index projecting system is combined with each of the right and left light paths of the observation optical system (photographing optical system)

Each the index projecting system has a light source 27a(27b) for projecting an index on the fundus of the eye 14, a pinhole index plate 28a(28b), which is disposed in a conjugate relation with the film 22a(22b), a relay lens 29a(29b) for projecting an index image of the index plate 28a(28b) on the fundus of the eye 14, a beam splitter 30a(30b) for synthesizing the index projecting system with the observing optical system. The index projecting light sources 27a and 27b are consisted of LEDs.

The light beams emitted from the light sources 27a and 27b pass through the pinhole of the index plates 28(28a, 28b) and the relay lenses 29(29a, 29b) and fall on the beam splitters 30(30a, 30b). The beam splitters 30(30a, 30b) reflect the light beams so that the light beams pass along the optical axis of the observation optical system. Then, the light beams pass along continuous lines as shown in FIG. 2 through the observing image forming lenses 24(24a, 24b), the mirrors 23(23a, 23b), the swing mirrors 20(20a, 20b), the focusing lenses 19(19a, 19b) and the relay lenses 18(18a, 18b) and perpendicularly on the flat surfaces of light beam splitting prisms 17(17a, 17b). The light beam splitting prisms 17(17a, 17b) and the light beam splitting prism 16 reflect the images so that the images pass through the openings of the two-hole diaphragm 15 and an objective lens 13 and fall on the fundus of the eye 14.

(b) Index detecting system

The index detecting system comprises a lens 31 for focusing the index images of the index plates 28a and 28b projected on the fundus and light receiving element 32 (with two elements 32a, 32b). The light receiving elements 32(32a, 32b) divided as shown in FIGS. 3(a) and 3(b) can be moved along the optical axis of the index projecting system together with the movement of the focusing lenses 19(19a, 19b) on the optical axis of the photographing optical system.

The index images reflected by the fundus of the eye 14 is focused at point A in an intermediate image by the objective lens 13 with a fundus image, and then reflected by the perforated mirror 12 toward the relay lens 11 and fall on the beam splitter 10.

Figure 4:
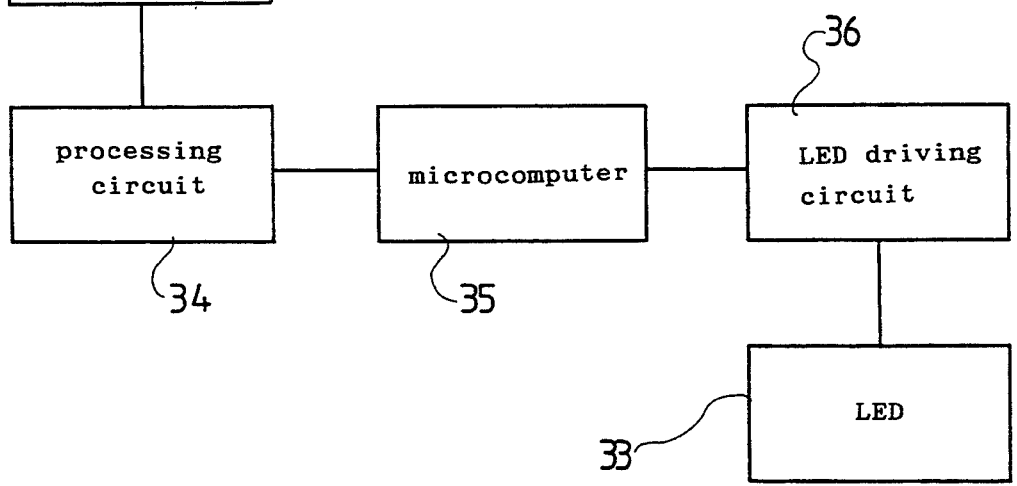
FIG. 4 is a block diagram of explaining a processing circuit of signal provided by the light receiving element.

The beam splitter 10 reflects the index images toward the light receiving elements 32, and the images are focused on the receiving surfaces of the light receiving elements 32(32a, 32b) by the lens 31. Signals of the light receiving elements 32(32a, 32b) are processed as mentioned below to detect the focus condition, the detected focusing condition is indicated to the photographer(observer) by a visible LED 33 on the basis of signals provided by the light receiving element 32, as shown in FIG. 4.

The operation of the stereoscopic retinal camera thus constructed will be described hereinafter.

The stereoscopic retinal camera is mounted on a movable table, not shown, which is moved relatively to a fixed table by a sliding mechanism. The examinee's head is held on a head support fixed to the fixed table, and the halogen lamp 1 is turned on to illuminate the eye 14. The joystick is operated to move the optical system by the sliding mechanism in various directions in order to align the image of the aperture diaphragm 6 formed on the cornea with the pupil of the eye 14, so that the fundus is illuminated properly.

The light beam reflected by the fundus is focused to form an inverted image of the fundus at the point A through the objective lens 13. The light beam passed the perforated mirror 12 is split into a right light beam and a left light beam by the two-hole diaphragm 15. The right light beam and the left light beam are interchanged by the light beam splitting prism 16 disposed directly behind the two-hole diaphragm 15, then, deflected by the prisms 17a and 17b, and focused in erect images of the fundus at the point B by a pair of image forming lens systems including the relay lenses 18a and 18b, the focusing lenses 19a and 19b, and the observation image forming lenses 24a and 24b. The observer views stereoscopically the erect images of the fundus through the oculars 25a and 25b.

The observer turns the focusing knob during the binocular observation of the images to focus the focusing lenses 19a and 19b and makes the fine adjustment of the alignment of the image of the aperture diaphragm 6 with the pupil of the eye 14 so that flares of the illuminating light will not appear around the right and left images.

The positions of the focusing lenses 19a and 19b are determined by the following procedure using the focusing detecting optical system.

Light beams emitted by the index projecting light source 27a and 27b pass through the pinholes of the index plates 28a and 28b are projected through the right and the left observing/photographing system on the fundus of the eye 14 in the image of the pinhole of the index plates 28a and 28b. The images of the pinhole of the index plates 28a and 28b reflected by the fundus pass through the objective lens 13 and reflected by the perforated mirror 12, pass through the relay lens 11 and fall on the beam splitter 10 of the index detecting system. The images reflected by the beam splitter 10 are focused by the relay lens 31 on the light receiving element 32.

When the respective positions of the focusing lenses 19a and 19b on the corresponding optical axes are adjusted so that the index plates 28a and 28b are in a conjugate relation with the fundus, the focusing lenses 19a and 19b are perfectly in focus. If the focusing lenses 19a and 19b are out of focus, the images of the pinholes of the index plates 28a and 28b formed on the fundus are blurred and split into two portions and, consequently, two images of the pinhole are formed on the sections 32A and 32B of the two-section light receiving element 32 as shown in FIG. 3(a). Since the sections 32A and 32B of the two-section light receiving element 32 are unbalanced in the quantity of incident light, the focusing lenses 19a and 19b are adjusted so that the two images coincide with each other in a sharp image of the pinhole on the two-section light receiving element 32 as shown in FIG. 3(b). In this state, the two sections 32A and 32B are balanced in the quantity of incident light.

Incidentally, if the focusing lenses 19a and 19b are further moved, the two images of the pinholes are again blurred and split into two portions and, accordingly, the two sections of the two-section light receiving element 32 are unbalanced in the quantity of incident light. Thus, by detecting the position at which the two images coincide with each other in a sharp image of the pinhole, the alignment may be perfectly determined.

Referring to FIG. 4 which shows the procedure of a control operation for processing signals provided by the two-section light receiving element 32, a signal processing circuit 34 compares signals which are provided by the two-section light receiving element 32 and, when the difference between the signals provided respectively by the two sections 32A and 32B of the two-section light receiving element 32 is smaller than a predetermined value, a microcomputer 35 drives a LED driving circuit 38 to turn on the LED 33 provided in the observing optical system to indicate that the focusing lenses 19a and 19b are in focus.

After the operations for aligning the image of the aperture diaphragm 6 with the pupil of the eye 14 and for focusing the focusing lenses 19a and 19b have been completed, a shutter release button is depressed. Then, the swing mirrors 20 is lifted up and the xenon flash lamp 3 flashes synchronously to form the image of the fundus on the film 22. The automatic operations of the stereoscopic retinal camera are controlled by the microcomputer inside the camera.

Thus, a pair of stereoscopic pictures of the fundus are obtained.

In the first embodiment, the LED 33 is turned on when the two sections 32A and 32B are balanced in the quantity of incident light, further the observation optical system may be combined with a display means to display a moving distance by which lenses 19a and 19b have to be moved. Since the alignment operation does not need strictly direct observation through a view finder, the observation optical system may use a TV monitor.

Each of the index plates 28a and 28b may be illuminated by a plurality of light sources. When the index projecting light sources 27a and 27b are infrared light sources and the light receiving element 32 is an infrared light receiving element, dazzling effect on the eye may be reduced. When infrared light sources are used, the images of the pinholes projected on the fundus are invisible, and the invisible images of the pinholes facilitate the observation and photographing of the fundus. In this case, if a beam splitter coated with only a coating for reflecting an infrared light is used, usually, it is not necessary to lower the light quantity of the illumination light.

Figure 5:
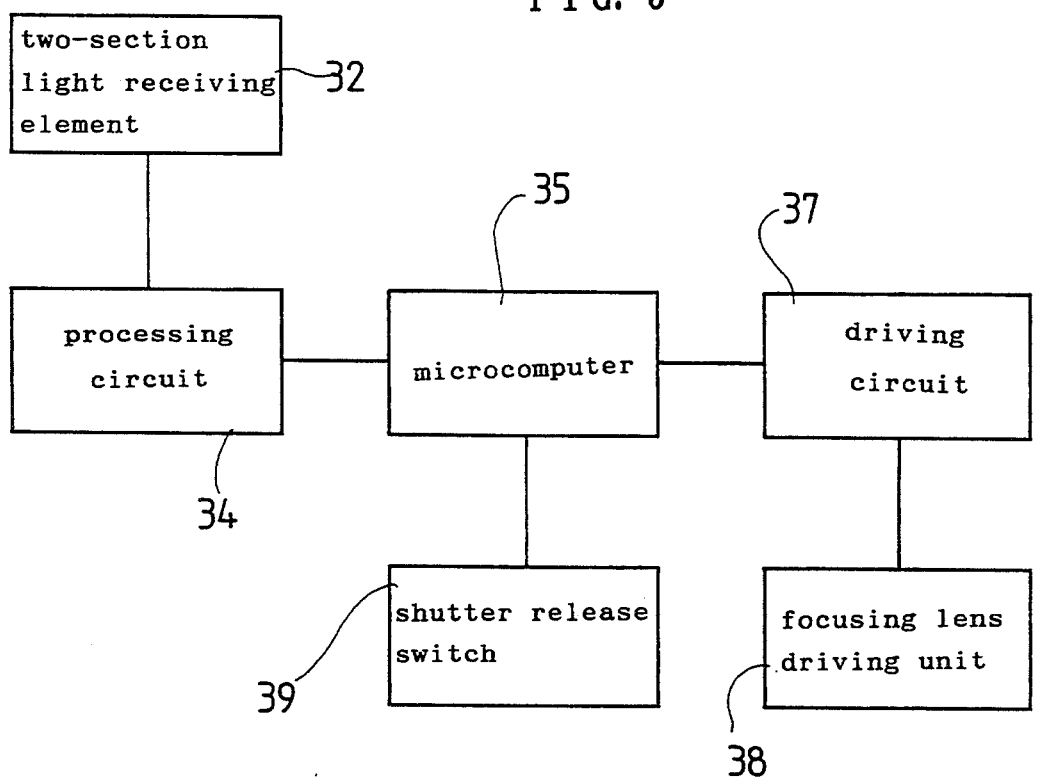
FIG. 5 is a block diagram of explaining an automatic control operation in a second embodiment according to the present invention.

A stereoscopic retinal camera in the second embodiment according to the present invention is similar in construction to the stereoscopic retinal camera in the first embodiment, except that the stereoscopic retinal camera in the second embodiment is provided with a control unit as shown in FIG. 5 which controls the stereoscopic retinal camera for automatic focusing operation.

Referring to FIG. 5, signals provided by the two sections 32A and 32B of the two-section light receiving element 32 are processed by a signal processing circuit 34 and the output signal of the signal processing circuit 34 is applied to a microcomputer 35. Then, the microcomputer 35 controls a focusing lens driving unit 38 through the driving circuit 37 to bring the focusing lenses 19a and 19b into focus. After the focusing lenses 19a and 19b have been focused, the microcomputer 35 turns on a shutter release switch 39 to take the picture of the fundus.

Instead of moving the light receiving element 32 as described in the above embodiment, the lens 31 of the index detecting system can be also moved according to the movement of the focusing lenses 19a and 19b.

In a stereoscopic retinal camera in the third embodiment, only the index detecting system of the focusing optical system having a different construction from in the first embodiment will be described with reference to FIGS. 6 and 7, and parts like or corresponding to those of the stereoscopic retinal camera in the first embodiment are denoted by the same reference characters and the description thereof will be omitted to avoid duplication.

(Focusing Detecting Optical System)

(b) Index Detecting System

Figure 3:
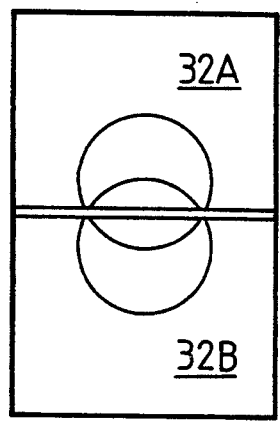
FIGS. 3(a) and 3(b) are views of showing index images formed on a light receiving element.
Figure 3:
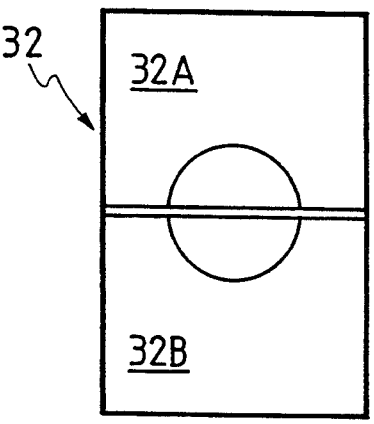

The index detecting system comprises a two-section light receiving element 32 having two sections 32A and 32B (as shown in FIG. 3), and a visible LED 33 for indicating the focusing condition on the basis of signals provided by the two-section light receiving element 32. The two-section light receiving element 32 is in a conjugate relation with a point B shown in FIG. 8.

The light beams reflected by the fundus are focused to form at a point A the images of the pinholes of the index plates 28a and 28b with the image of the fundus, and then pass through the central opening of the two-hole diaphragm 15, the relay lens 40, a focusing lens 19c and an image forming lens 31, and fall on the sections 32A and 32B of the two-section light receiving element 32 to form the images of the pinholes, i.e., the indices.

The focusing lens 19c is moved together with the focusing lenses 19a and 19b, instead of moving the light receiving element 32 as described in the first embodiment.

The stereoscopic retinal camera in the third embodiment may be provided with the control unit of the stereoscopic retinal camera for automatic focusing similarly in the second embodiment.

A stereoscopic retinal camera in a fourth embodiment according to the present invention, which has a different construction of the focusing detecting optical system from in the first and third embodiments, will be described with reference to FIGS. 8 and 9, in which parts like or corresponding to those of the stereoscopic retinal camera in the first embodiment are denoted by the same reference characters and the description thereof will be omitted.

(Focusing Detecting Optical System)

Figure 8:
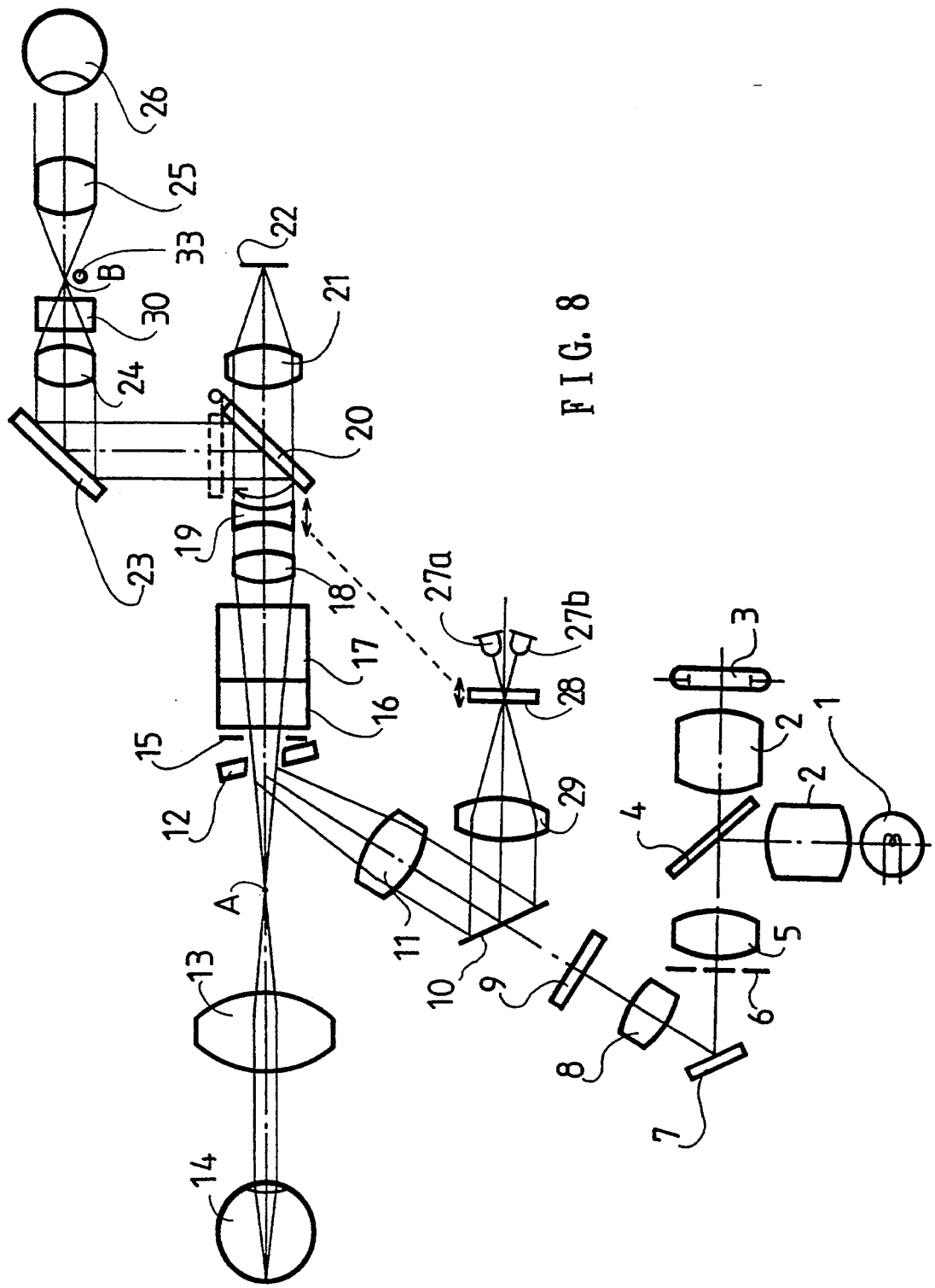
FIG. 8 is a diagrammatic view of an optical system in a fourth embodiment according to the present invention, except for an index detecting system.
Figure 9:
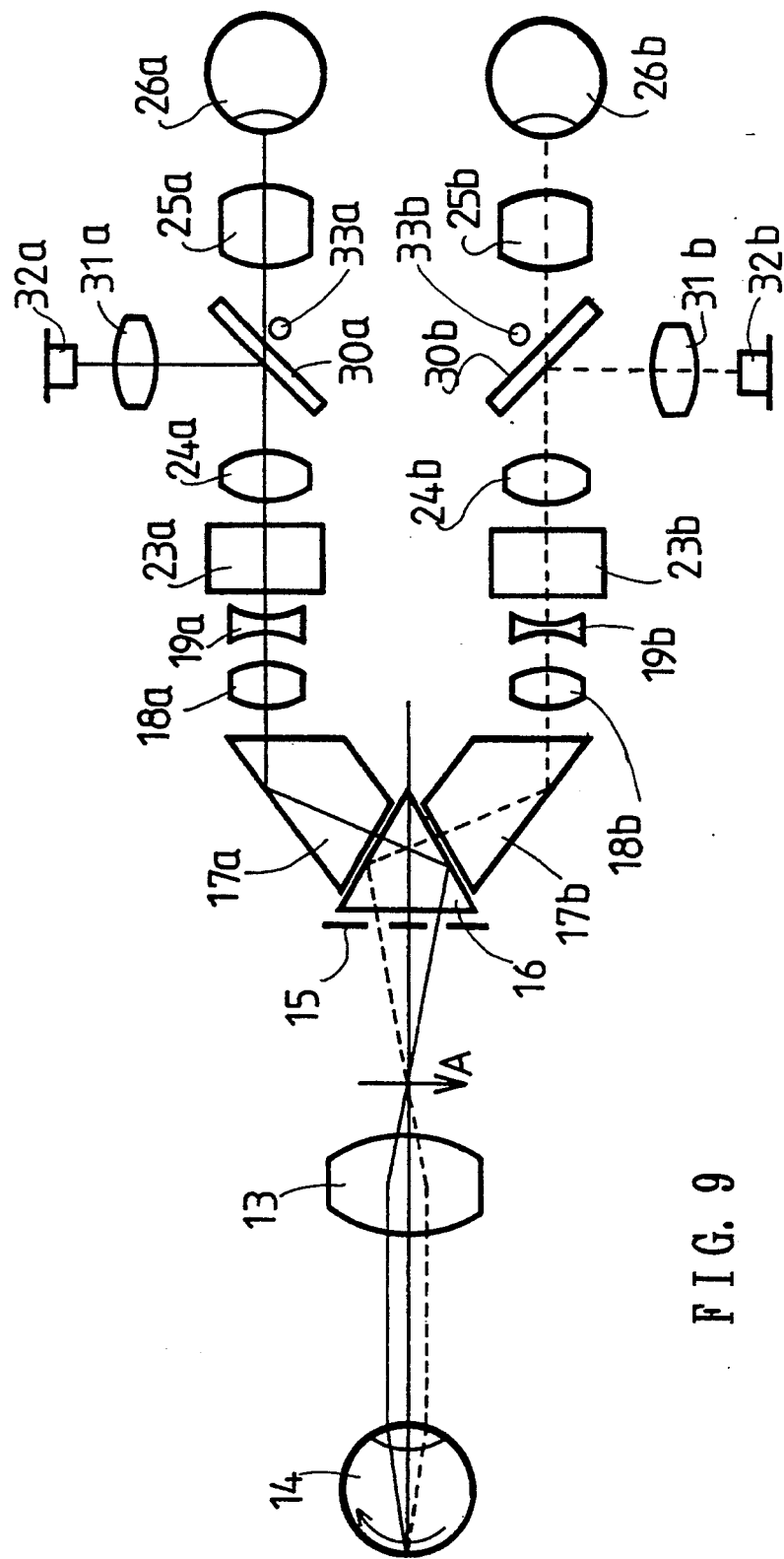
FIG. 9 is a diagrammatic top view of the optical system f of FIG. 8.

Referring to FIGS. 8 and 9, a focusing detecting optical system consists of an index projecting system and an index detecting system.

(a) Index Projecting System

The index projecting system is combined with the light path of the illumination optical system and comprises index projecting light sources 27a and 27b, index plate 28, which is in a conjugate relation with a film 22, relay lens 29 through which the image of the pinhole of the index plate 28 is projected on the fundus of the eye 14, and a beam splitter 10, which combines the index projecting system with the illumination optical system. The image of the pinhole of the index plate 28 reflected by the beam splitter 10 passes through the relay lens 11 which is a component of the illumination optical system, and fall perpendicularly on the perforated mirror 12. The image reflected by the perforated mirror 12 is focused at A point in an intermediate image to form an image on the fundus through an objective lens 13.

(b) Index Detecting System

The index detecting system is combined with a right and a left light paths of the observing optical system and comprises image forming lenses 31a and 31b, two-section light receiving elements 32a and 32b, and visible LEDs 33a and 33b for indicating focusing condition on the basis of signals provided by the two-section light receiving elements 32a and 32b.

The index images reflected by the fundus of the eye 14 is focused at A point in an intermediate image by the objective lens 13 with an image of the fundus, and pass through the opening of the perforated mirror 12 and is split into a right light beam and a left light beam by the two-hole diaphragm 15. The light beam splitting prism 16 interchanges the right light beam and the left light beam, then, the light beams are deflected by the prisms 17a and 17b, and pass through the relay lenses 18a and 18b, the focusing lenses 19a and 19b, and the observing image forming lenses 24a and 24b, and reflected by the beam splitters 30a and 30b. The images reflected by the beam splitters 30a and 30b pass through the image forming lenses 31a and 31b, and are focused on the light receiving sections of each of the light receiving elements 32a and 32b to form the images of the index. The detected focusing conditions are indicated to the photographer(observer) by the visible LEDs 33a and 33b on the basis of signals provided by the light receiving elements 32a and 32b.

In the above embodiment, the balance in the quantity of incident light is detected on the basis of signals provided by the light receiving elements 32a and 32b, further may be detected based on the blurred condition of the images of the pinholes of the index plates 28 formed on the fundus.

The photographer(observer) turns the focusing knob during the binocular observation of the images to focus the focusing lenses 19a and 19b, and the positions of the focusing lenses 19a and 19b are determined by the following procedure using the focusing detecting optical system.

The index plate 28, disposed in a conjugate relation with the film 22(and the receiving sections of the light receiving elements 32a and 32b) to the fundus of the eye 14, is movable on the optical axis together with the focusing lenses 19a and 19b.

Light beams emitted by the index projecting light sources 27a and 27b pass through the pinhole of the index plate 28 and the relay lense 29, and an objective lens and the like to be projected on the fundus.

When the respective positions of the focusing lenses 19a and 19b on the corresponding optical axes are adjusted so that the index plate 28 is in a conjugate relation with the fundus, the focusing lenses 19a and 19b are perfectly in focus. If the focusing lenses 19a and 19b are out of focus, the image of the pinhole of the index plate 28 formed on the fundus is blurred and split into two portions and, consequently, two images of the pinhole are formed on the sections 32A and 32B of each of the light receiving elements 32a and 32b (referring to FIG. 3(a)). When the light sources 27a and 27b alternately is turned on, the sections A and B of each of the light receiving elements 32a and 32b are unbalanced in the quantity of incident light. At a coincide position of the images of the pinhole of the index plate 28, the two sections A and B are balanced in the quantity of incident light.

Signals provided by the light receiving elements 32a and 32b are respectively compared at a signal processing circuit 34, and when the difference between the signals provided respectively by the sections 32A and 32B of each of the light receiving element 32a and 32b is smaller than a predetermined value, a microcomputer 35 drives a LED driving circuit 36 to turn on LEDs 33a and 33b provided in the observing system to indicate that the focusing lenses 19a and 19b are in focus, according to the control operation shown in FIG. 4.

When right and left optical axes of photographing optical system are in each decentering condition different from the cornea and the crystal line lens of the examinee's eye, the right and left photographing optical systems have respectively the best focus position different from each other. The photographer adjusts the focusing lenses 19a and 19b, in consideration of both conditions of index images observed through the observing optical system and LEDs 33a and 33b, so that the most proper focus conditions of both photographing optical systems can be detected.

In the fourth embodiment, the focusing conditions of the right and the left optical system are respectively detected and indicated by the LEDs 33a and 33b, also may be indicated by one focus point to be provided by comparing both signals of the light receiving elements 32a and 33b. The focus point may be determined by various methods, for instance, smoothing signals provided by the light receiving elements 32a and 32b when the focusing lenses 19a and 19b are moved, and selecting a focus point with higher signal level.

Figure 10:
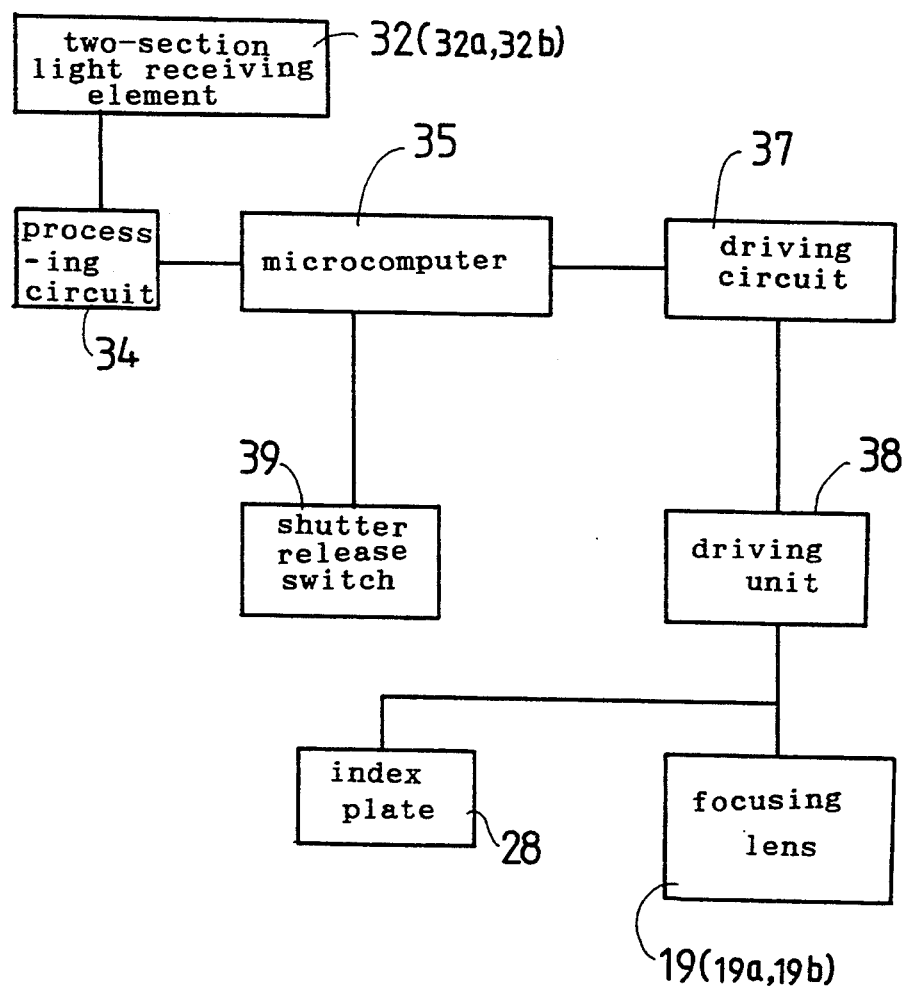
FIG. 10 is a block diagram of explaining an automatic control operation in a fifth embodiment according to the present invention.
Figure 11:
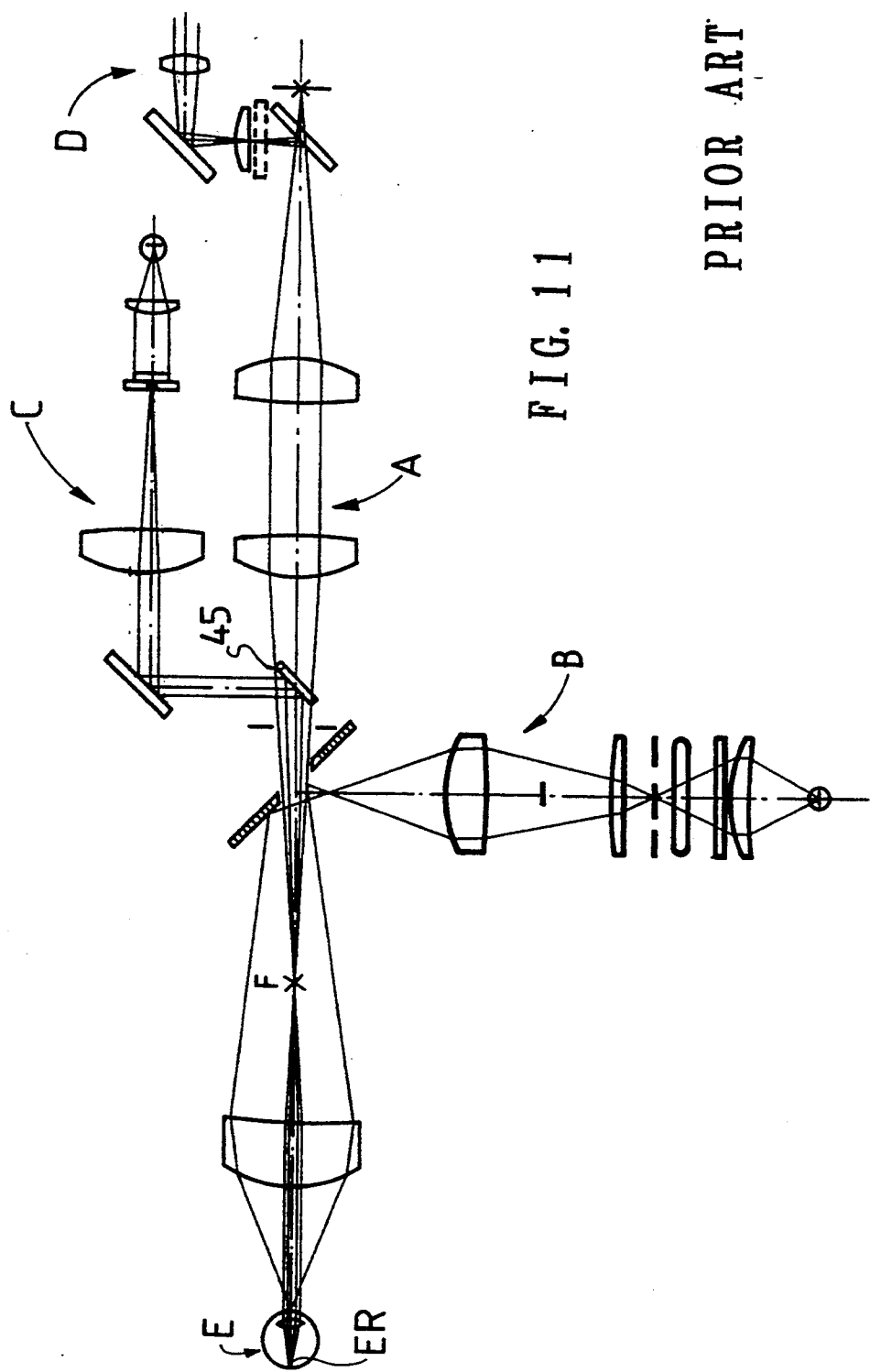
FIG. 11 is a schematic diagram of an optical system of a prior art retinal camera.
Figure 12:
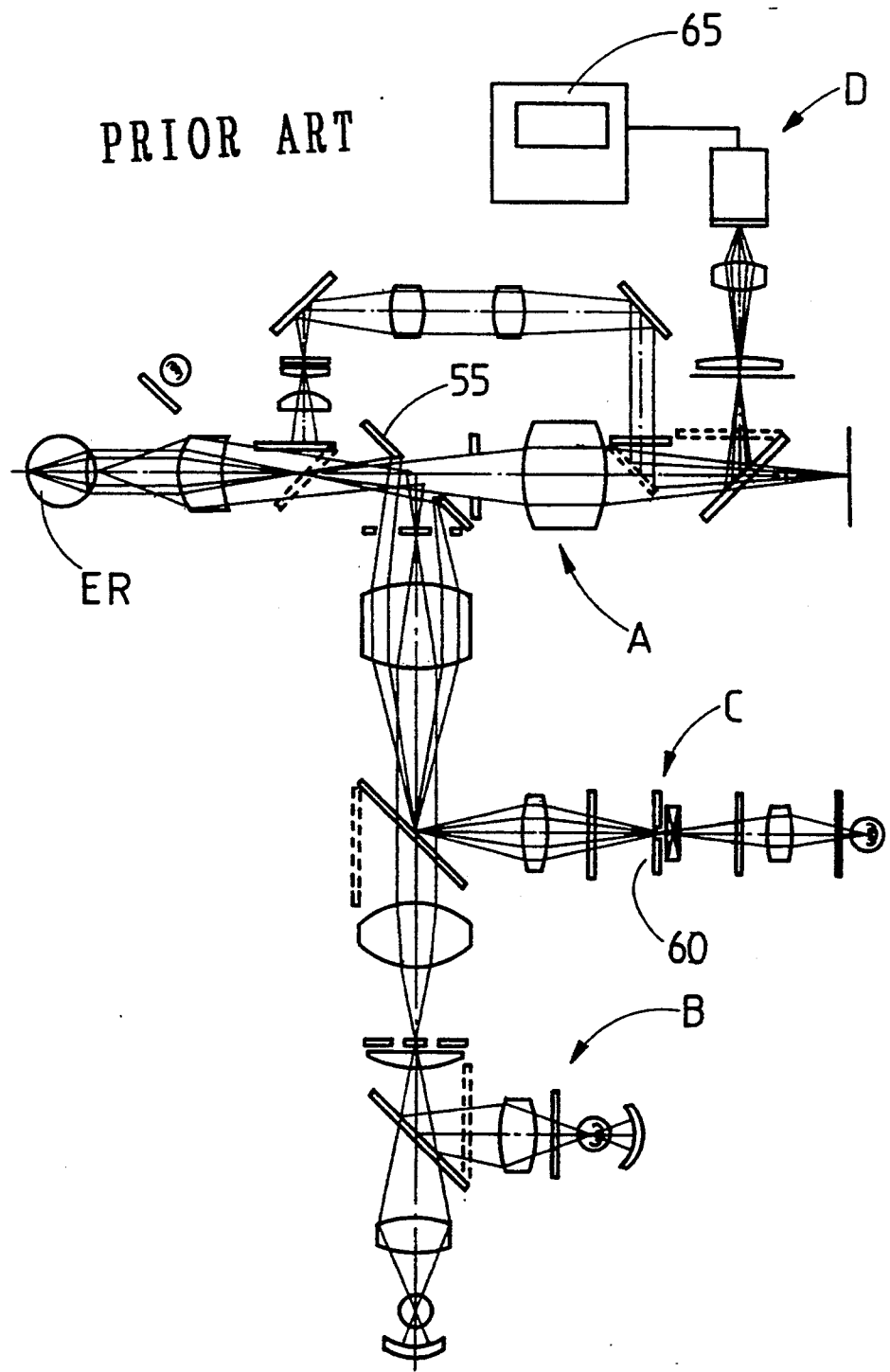
FIG. 12 is a schematic diagram of an optical system of another prior art retinal camera.

A stereoscopic retinal camera in a fifth embodiment according to the present invention is similar in construction to the stereoscopic retinal camera in the fourth embodiment, except that the stereoscopic retinal camera in the fifth embodiment is provided with a control unit as shown in FIG. 10 which controls the stereoscopic retinal camera for automatic focusing operation.

Referring to FIG. 10, signals provided by the light receiving elements 32a and 32b are processed by a signal processing circuit 34 and the output signal of the signal processing circuit 34 is applied to a microcomputer 35. Then, the microcomputer 35 determines a focus point by using one of the above determining methods, and controls a driving unit 38 through a driving circuit 37 according to the predetermined focus point to bring and the index plate 28 and the focusing lenses 19a and 19b into focus. After the focusing lenses 19a and 19b have been focused, a shutter release switch 39 comes into a condition capable of photographing and the photographer can turn on it to take a picture of the fundus, or automatically the microcomputer 35 turns on a shutter release switch 39 to take the picture of the fundus.

In the fifth embodiment, modifications and variations described in the fourth embodiment may be also utilized. And further, the index projecting system may be constructed of two independent index projecting systems changeable each projecting distance and movable according to each of the focusing lenses 19a and 19b. Such index projecting systems may be also applied to the fourth embodiment.

The optical system of the stereoscopic retinal camera in the fourth and fifth embodiments is similar to the optical system in the first embodiment corresponding to FIGS. 1 and 2, but the index projecting system and the index detecting system of the focus detecting optical system are interchanged in FIGS. 8 and 9, namely, the index detecting system is combined with a right and a left light paths of the observing optical system. Accordingly, in the fourth and fifth embodiments, respective focus conditions can be observed through the right and left photographing optical systems.

Figure 6:
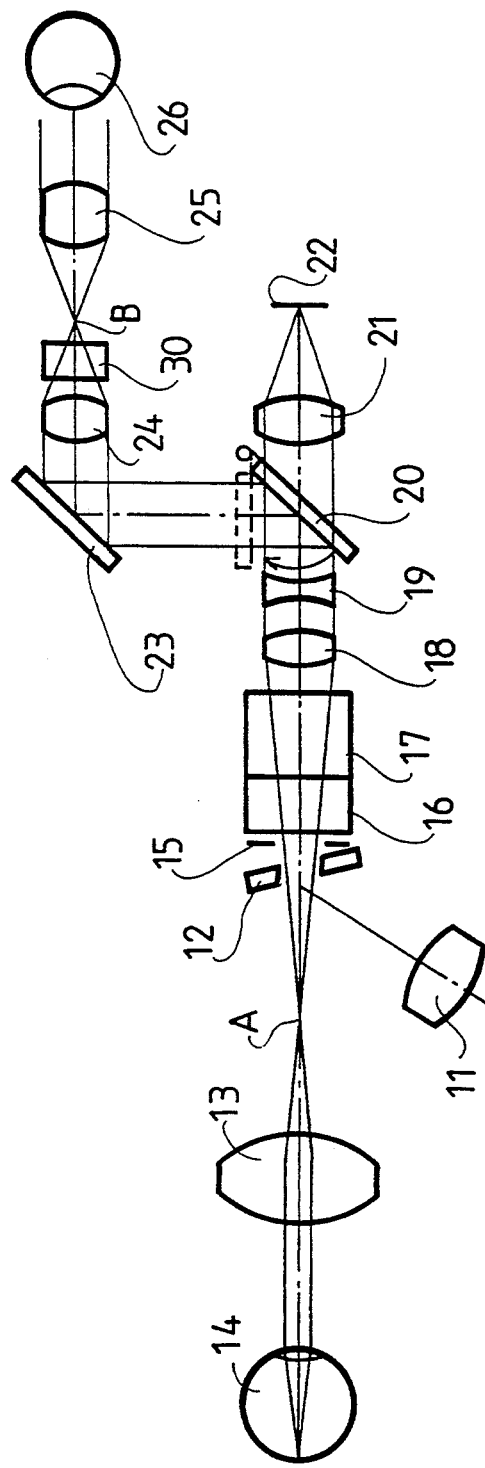
FIG. 6 is a diagrammatic side view of the optical system in a third embodiment according to the present invention.
Figure 6:
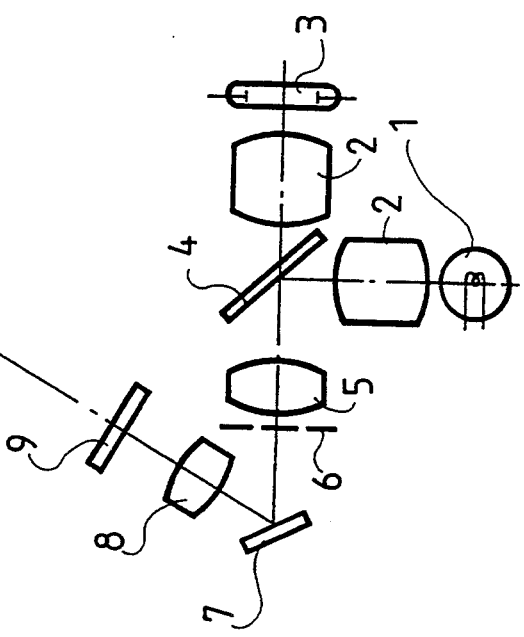
Figure 7:
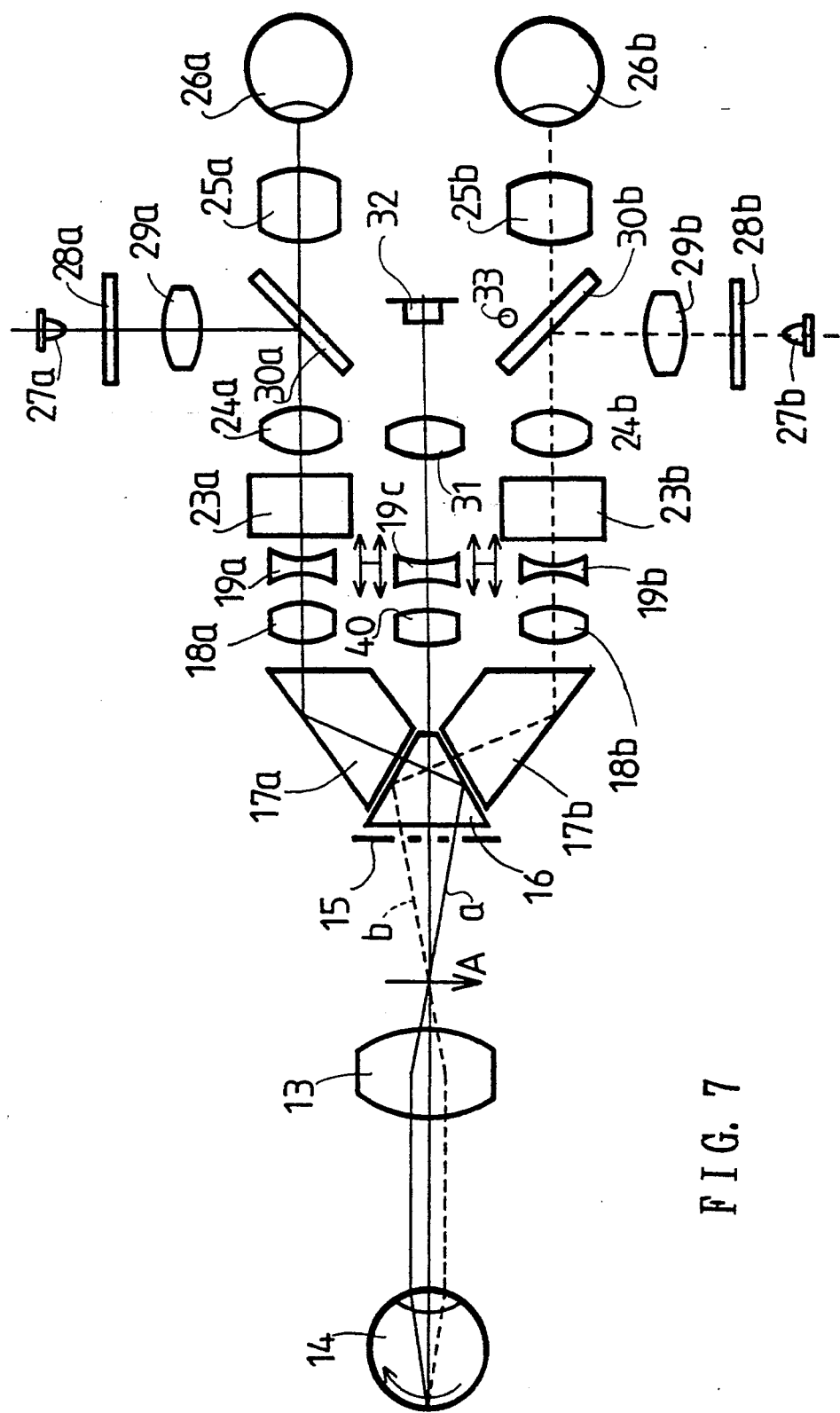
FIG. 7 is a diagrammatic top view of the optical system of FIG. 6.

It is obvious that the arrangement of the focus detecting optical system mentioned above can similarly be applied to the third embodiment corresponding to FIGS. 6 and 7, and which is within the scope of the present invention.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A stereoscopic retinal camera comprising:
   an illumination optical system for illuminating the fundus of an examinee's eye;
   an observing/photographing optical system for observing and photographing an image of the fundus of the eye in a stereoscopic picture, and comprising,
   (a) a light beam splitting optical system for splitting the light beam of the illumination optical system reflected by the fundus into a right light beam and a left light beam, and
   (b) a pair of image forming optical systems for forming respective images of the fundus by the two light beams;
   an index projecting optical system for projecting a focusing index on the examinee's eye;
   an index detecting optical system for detecting the focusing condition of the focusing index projected on the fundus of the eye;
   a judging means for judging a focusing condition by processing signals provided by said index detecting optical system;
   wherein one of said index projecting optical system and the index detecting optical system comprises a pair of right and left optical systems, said right and left optical systems are each disposed on a light path branched from a light path of said image forming optical systems by a reflecting mirror for reflecting a light beam of the focusing index.

2. A stereoscopic retinal camera according to claim 1, wherein the pair of right and left optical systems are provided in the index projecting optical system, and said judging means judges a focusing condition on the basis of a positional relation between a pair of focusing indices detected by said index detecting optical system.

3. A stereoscopic retinal camera according to claim 2, wherein said index detecting optical system is disposed on a light path branched from the light path of the illumination optical system.

4. A stereoscopic retinal camera according to claim 2, wherein said index detecting optical system detects the images of the index passing through the opening of a two-hole diaphragm of said light splitting means.

5. A stereoscopic retinal camera according to claim 2, wherein said index detecting optical system comprises a photodetector consisted of a plurality of light receiving elements to receive the images of the focusing index reflected by the fundus of the eye, and a photodetector moving means for moving the photodetector along the optical axis of the index detecting optical system according to the movement of a focusing lens disposed on the optical path of said observing/photographing optical systems.

6. A stereoscopic retinal camera according to claim 5, further comprising an indicating means for indicating that said plural light receiving elements are balanced in the quantity of incident light on the basis of signals provided by the light receiving elements.

7. A stereoscopic retinal camera according to claim 5, further comprising an automatic focusing control means for moving said focusing lens along the optical axis of the observing/photographing optical system if the images of the focusing index formed on said plural light receiving elements are out of focus, and for stopping of the movement of the focusing lens when the images of said focusing index are in focus.

8. A stereoscopic retinal camera according to claim 2, wherein said index detecting optical system comprises a plurality of light receiving elements to receive the image of the focusing index reflected by the fundus, a focusing movable lens for focusing the image of the focusing index to be detected by the plural light receiving elements, and further a focusing movable lens moving means for moving the focusing movable lens along the optical axis of the detecting optical system according to the movement on the optical axis of the focusing lens disposed on the optical path of the observing/photographing optical system.

9. A stereoscopic retinal camera according to claim 8, further comprising an indicating means for indicating that said plural light receiving elements are balanced in the quantity of incident light on the basis of signals provided by the light receiving elements.

10. A stereoscopic retinal camera according to claim 8, further comprising an automatic focusing control means for moving said focusing lens along the optical axis of the observing/photographing optical system if the images of the focusing index formed on said plural light receiving elements are out of focus, and for stopping of movement of the focusing lens when the images of the focusing index are in focus.

11. A stereoscopic retinal camera according to claim 1, wherein a pair of right and left optical systems are provided in the index detecting optical system, and said index projecting optical system is disposed on an optical path branched from the optical path of the illumination optical system by a light path dividing mirror.

12. A stereoscopic retinal camera according to claim 11, wherein said index detecting optical system comprises a photodetector consisted of a plurality of light receiving elements to receive the image of the focusing index reflected by the fundus of the eye, and an optical distance changing means for changing an optical distance from the fundus of the examinee's eye to the photodetector by moving the photodetector according to the movement of a focusing lens disposed on the optical path of said observing/photographing optical system.

13. A stereoscopic retinal camera according to claim 12, further comprising a driving means for driving the focusing lens of the observing/photographing optical system on the basis of the focusing condition of the focusing index detected by said photodetector.

14. A stereoscopic retinal camera comprising:
an illumination optical system for illuminating the fundus of an examinee's eye;
an observing/photographing optical system for observing and photographing an image of the fundus of the eye in a stereoscopic picture, and comprising,
(a) a light beam splitting optical system for splitting the light beam of the illumination optical system reflected by the fundus into a right light beam and a left light beam, and
(b) a pair of image forming optical systems for forming respective images of the fundus by the two light beams;
an index projecting optical system for projecting a focusing index on the examinee's eye;
an index detecting optical system for detecting the focusing condition of the focusing index projected on the fundus of the eye;
a judging means for judging a focusing condition by processing signals provided by said index detecting optical system;
wherein one of said index projecting optical system and the index detecting optical system comprises a pair of right and left optical systems, said right and left optical systems are each disposed on a light path branched from light paths of said image forming optical system, and use a part of the light paths of the image forming optical system in common with a reflecting mirror for reflecting the images of the index;
wherein a pair of right and left optical systems are provided in the index detecting optical system, and said index projecting optical system is disposed on an optical path branched from the optical path of the illumination optical system by a light path dividing mirror; and
wherein the index projecting optical system comprises a plurality of index projecting light sources and a pinhole index, said pinhole index is disposed in a conjugate relation with an imaging device of the observing/photographing optical system.

15. A stereoscopic retinal camera according to claim 14, wherein the index detecting optical system comprises plural divided light receiving elements to receive the images of the focusing index reflected by the fundus of the eye, and an indicating means for indicating that said plural light receiving elements are balanced in the quantity of incident light on the basis of signals provided by the light receiving elements.

16. A stereoscopic retinal camera according to claim 15, wherein said indicating means is provided in each of a pair of right and left detecting optical systems.

17. A stereoscopic retinal camera according to claim 14, wherein light sources and a pinhole of the index projecting optical system are adjusted so that a plurality of pinhole images formed on the fundus with a plurality of index projecting light sources are in correspondence when focused.

* * * * *